United States Patent [19]

Henning et al.

[11] Patent Number: 4,470,989
[45] Date of Patent: Sep. 11, 1984

[54] NEUROLEPTIC N-OXACYCLYL-ALKYLPIPERIDINE DERIVATIVES

[75] Inventors: Rainer Henning, Frankfurt am Main; Rudolf Lattrell, Königstein; Hermann Gerhards, Hofheim am Taunus, all of Fed. Rep. of Germany

[73] Assignee: Hoechst Aktiengesellschaft, Frankfurt am Main, Fed. Rep. of Germany

[21] Appl. No.: 389,677

[22] Filed: Jun. 18, 1982

[30] Foreign Application Priority Data

Jun. 20, 1981 [DE] Fed. Rep. of Germany ....... 3124366

[51] Int. Cl.³ .................. A61K 31/445; C07D 405/14
[52] U.S. Cl. ..................................... 424/267; 546/197; 546/199
[58] Field of Search ................. 546/199, 197; 424/267

[56] References Cited

U.S. PATENT DOCUMENTS 4,329,348  5/1982  Huebner .............................. 424/251

FOREIGN PATENT DOCUMENTS 5610   11/1979  European Pat. Off. .
4358    1/1982  European Pat. Off. ............ 546/199
2213059  8/1974  France ................... 546/199
2361889  3/1978  France ................... 546/199

OTHER PUBLICATIONS

Chem. Abstr., 84, 31059q, (1976), [Japan. Kokai 75 84,579, Ueno et al., 7/8/75].
Chem. Abstr., 84, 31060h, (1976), [Japan. Kokai 75 84,578, Sato et al., 7/8/75].
Chem. Abstr., 91, 168329s, (1976), [Costall et al., J. Pharm. Pharmacol., 1978, 30, (11), 693–8].
Janssen, P. et al., Arzneim.-Forsch., 15, 104, (1965).

Primary Examiner—Richard A. Schwartz

[57] ABSTRACT

Neuroleptically active compounds of the formula

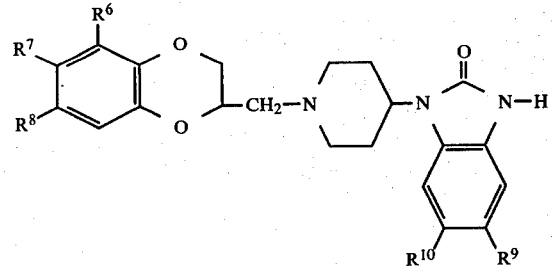

wherein $R^6$ and $R^{10}$ are —H or $CH_3$; $R^7$ and $R^8$ are independently —H, —F, —Cl, or —$CH_3$; and $R^9$ is —F, —Cl, —$CH_3$, or —$OCH_3$.

8 Claims, No Drawings

NEUROLEPTIC N-OXACYCLYL-ALKYLPIPERIDINE DERIVATIVES

The invention relates to new compounds of the general formula I

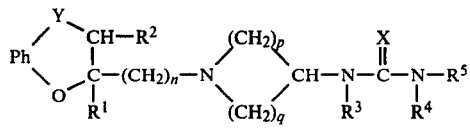

in which n denotes one, two or three; p and q denote integers from one to three, (p+q) being the number four; Ph denotes unsubstituted 1,2-phenylene or 1,2-phenylene which carries one to three identical or different and independent substituents, possible substituents being straight-chain or branched alkyl with 1 to 6 carbon atoms, alkoxy with 1 to 4 carbon atoms, alkylenedioxy with 1 or 2 carbon atoms, halogen, trifluoromethyl, nitro or alkanoyl with 1 to 3 carbon atoms; $R^1$ and $R^2$ are identical or different and independent, and denote hydrogen or alkyl with 1 to 5 carbon atoms; $R^3$ and $R^4$ are identical or different and independent, and denote hydrogen or alkyl with 1 to 5 carbon atoms, or $R^3$ and $R^4$ together denote Ph', which has the meanings of Ph but is independent thereof, or together denote straight-chain or branched alkylene with 1 to 5 carbon atoms; $R^5$ denotes hydrogen, alkyl with 1 to 5 carbon atoms, or phenyl which is optionally monosubstituted or disubstituted by straight-chain or branched alkyl with 1 to 6 carbon atoms, alkoxy with 1 to 4 carbon atoms, alkylenedioxy with 1 or 2 carbon atoms, halogen, trifluoromethyl, nitro or alkanoyl with 1 to 3 carbon atoms; X denotes an oxygen or sulfur atom, imino or alkylimino with 1 to 4 carbon atoms; and Y denotes an oxygen or sulfur atom or a sulfinyl group.

Preferred compounds of the formula I are those in which n denotes one, two or three; p and q denote two; Ph denotes unsubstituted 1,2-phenylene or 1,2-phenylene which carries one or two identical or different and independent substituents from the following group; alkyl with 1 to 4 carbon atoms, alkoxy with 1 to 3 carbon atoms, alkylenedioxy with 1 or 2 carbon atoms, halogen, trifluoromethyl, nitro, formyl and acetyl; $R^1$ and $R^2$ are identical or different and independent, and denote hydrogen, methyl, ethyl, propyl or isopropyl; $R^3$ and $R^4$ are identical or different and independent, and denote hydrogen, methyl or ethyl, or $R^3$ and $R^4$ together denote Ph', defined as Ph above, or together denote alkylene with 2 to 4 carbon atoms; $R^5$ denotes hydrogen, methyl, ethyl, propyl, butyl, isopropyl, isobutyl, phenyl or p-tolyl; X denotes an oxygen or sulfur atom, an imino group or an alkylimino group with 1 to 4 carbon atoms; and Y denotes an oxygen or sulfur atom.

Particularly preferred compounds of the formula I are those in which n denotes one; p and q denote two; Ph denotes unsubstituted 1,2-phenylene or 1,2-phenylene which is substituted by methyl, ethyl, methoxy, ethoxy, methylenedioxy, 1,2-ethylenedioxy, chlorine, bromine, fluorine, trifluoromethyl, nitro, formyl or acetyl; $R^1$ and $R^2$ denote hydrogen; $R^3$ and $R^4$ are identical or different and independent, and denote hydrogen, methyl or ethyl, or $R^3$ and $R^4$ together denote Ph', defined as Ph above; $R^5$ denotes hydrogen, methyl or ethyl; X denotes an oxygen or sulfur atom or an imino or methylimino group; and Y denotes an oxygen atom.

The invention relates to the free bases of the formula (I) and salts thereof with physiologically acceptable acids. Possible acids are: mineral acids such as hydrochloric and hydrobromic acid and sulfuric, phosphoric, nitric or perchloric acid, and organic acids, such as formic, acetic, propionic, succinic, glycolic, lactic, malic, tartaric, citric, maleic, fumaric, phenylacetic, benzoic, methanesulfonic, toluenesulfonic, oxalic, 4-aminobenzoic or ascorbic acid.

The compounds according to the invention, of the formula

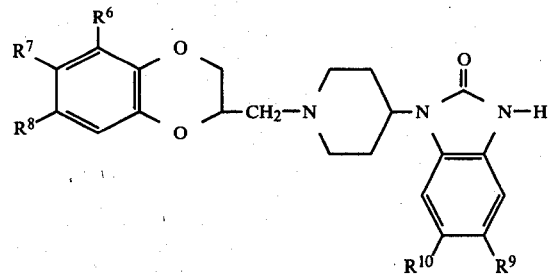

in which $R^6$ denotes hydrogen or methyl, $R^7$ and $R^8$ independently of one another denote hydrogen, fluorine, chlorine or methyl, $R^9$ denotes fluorine, chlorine, methyl or methoxy and $R^{10}$ denotes hydrogen or methyl, and especially those compounds in which $R^6$, $R^7$ and $R^{10}$ denote hydrogen, $R^8$ denotes hydrogen or fluorine and $R^9$ denotes fluorine, chlorine, methyl or methoxy, are of particular interest.

The invention furthermore relates to a process for the preparation of the compounds of the formula (I), which comprises (1) subjecting a reactive ester of an oxacyclic alkanol of the general formula (II) to condensation with a piperidine derivative of the general formula (III).

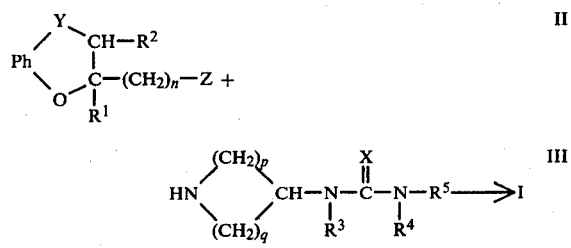

Ph, Y, $R^1$ and $R^2$ in formula (II) and p, q, X, $R^3$, $R^4$ and $R^5$ in formula (III) have the same meanings as in formula (I). The radical Z in formula (II) represents halogen, such as chlorine, bromine or iodine, or a reactive ester group, such as the sulfuric acid radical or the p-toluenesulfonyl, m-bromobenzenesulfonyl, p-nitrobenzenesulfonyl, methanesulfonyl or trifluoromethanesulfonyl group.

Another process comprises (2) reacting a compound of the formula (IV)

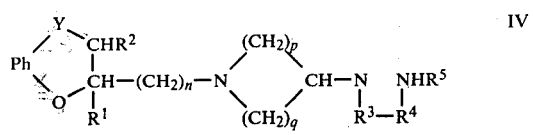

with a reactive carbonic acid derivative, all the substituents and symbols having the abovementioned meanings, but $R^3$ and $R^4$ together denoting alkylene or Ph'.

Compounds of the formula (I) in which $R^3$ and $R^4$ do not link the nitrogen atoms carrying them via a bridge are obtained by a variant of this process:

A compound of the formula (V)

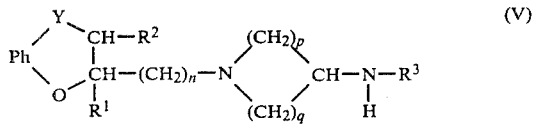

in which n, p, q, Ph, $R^1$, $R^2$, $R^3$ and Y are as defined for formula (I), is first reacted with a reactive carbonic acid derivative, and the product is then reacted with a compound of the formula (VI)

in which $R^4$ and $R^5$ are as defined for formula (I).

Another variant comprises reversing the sequence of the reaction steps, ie. first reacting a compound of the formula (VI) with the carbonic acid derivative and then reacting the product with a compound of the formula (V).

Finally, a mixture consisting of a compound of the formula (V) and a compound of the formula (VI) is also reacted with a reactive carbonic acid derivative to give the compounds of the formula (I) according to the invention.

In the present invention, by reactive carbonic acid derivatives there are understood ammonium cyanate or thiocyanate, a metal cyanate or thiocyanate, a cyanogen halide, a cyanamide which is optionally substituted by alkyl with 1 to 4 carbon atoms, carbon disulfide or carbonyl sulfide, a carbonic acid halide, a thiocarbonic acid halide, a chlorocarbonic acid alkyl, benzyl or phenyl ester, a carbonic acid dialkyl, dibenzyl or diphenyl ester, urea, thiourea, 1,1-carbonyldiimidazole, an O-alkylisourea, an S-alkylisothiourea and guanidine.

The condensation in process (1) is carried out in an organic solvent, such as methanol, ethanol, toluene, dioxane, tetrahydrofuran, pyridine, dimethylsulfoxide or dimethylformamide, preferably in the presence of a basic condensing agent. Possible condensing agents are alkali metal and alkaline earth metal hydroxides, carbonates and bicarbonates, and also alkali metal hydrides, alkoxides and alkanoates as well as organic tertiary nitrogen bases, such as triethylamine, tripropylamine, N-methylmorpholine or lutidine. The reaction temperature is usually 0° C. to 180° C., preferably 20° to 100° C.

Process (2) is carried out in a manner which is known per se, without a solvent or in an organic solvent or a mixture consisting of an organic solvent and water. If the reactive carbonic acid derivative is an ammonium or metal thiocyanate or cyanate, possible solvents are those which are polar and water-miscible, such as methanol, ethanol, acetone, tetrahydrofuran, dioxane, dimethylformamide and dimethylsulfoxide, and mixtures thereof with water.

In all other cases, possible solvents are those anhydrous solvents just mentioned, and in addition toluene, xylene, glycol dimethyl ether, diglycol dimethyl ether, triglycol dimethyl ether, pyridine and sulfolane. In addition, a basic condensing agent can be added to remove the acid liberated. Preferred possible condensing agents are those mentioned in the case of process (1).

The starting materials for the processes described are prepared by methods which are known from the literature. If n denotes one, the compounds of the formula (II) are obtained from a substituted pyrocatechol or o-mercaptophenol by reaction with epichlorohydrin and subsequent conversion of the oxacyclyl-alkanol thus obtained into the reactive ester with the aid of a strong acid or a derivative thereof, such as thionyl chloride, a phosphorus halide or a benzenesulfonyl halide (J. Med. Chem. 8, 446 (1965)). If n denotes two or three, a suitable 1,4-benzodioxan-2-yl-carboxylic acid is reduced to the corresponding alcohol by a process similar to that described in European Patent Application No. 4358, for example using lithium aluminum hydride or sodium 2-methoxyethoxy aluminum hydride, and the esterification is then carried out as described above.

Compounds of the formula (III) can be prepared, for example, as described in German Offenlegungsschrift No. 2,526,393 or German Offenlegungsschrift No. 2,400,094, starting from aminopiperidine which is protected in the 1-position by a carbethoxy or benzyl group and a suitably substituted o-chloronitrobenzene, with subsequent catalytic hydrogenation of the nitro group to the amino group, for example using Raney nickel as the catalyst, cyclization with a carbonic acid derivative analogously to process (2), and splitting off of the amino-protective group in the 1-position.

Compounds of the formula (IV) are obtained by reacting compounds of the formula (II) with compounds of the formula (VII)

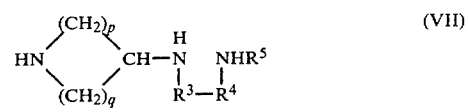

which are obtained as intermediates in the preparation of the starting materials of the formula (III). The reaction conditions for this reaction are the same as those described for process (1).

In the text which follows, percentages are by weight, unless otherwise indicated.

The compounds of the formula (I) according to the invention have pharmacological actions, in particular antipsychotic (neuroleptic) actions. Thus, they antagonize amphetamine aggregation toxicity in mice as a function of the dose. In this test, groups of 10 mice each which are kept in a small area (about 25 cm²/mouse) are subcutaneously injected with 20 mg/kg of D-amphetamine in 0.2% strength aqueous solution one hour after administration of a compound of the formula (I). The dose of compound (I) which protects 50% of the animals from death by amphetamine poisoning is determined. The $ED_{50}$ values of the compounds of the formula (I) are between 0.01 and 40 mg/kg. Furthermore, the compounds inhibit the stereotype behavior caused in rats by amphetamine and apomorphine. The action is determined by conventional statistical methods; using these, the $ED_{50}$ values for these tests are calculated. For compounds of the formula (I) they are 0.1 to 20 mg/kg, preferably up to 5 mg/kg, for inhibition of amphetamine-induced stereotypie and 0.01 to 20 mg/kg, preferably up to 5 mg/kg, for inhibition of apomorphine-induced stereotypie.

In another experiment, a one-sided cerebral lesion is produced in rats, after which the animals, after administration of amphetamine, rotate on their axis in the direction of the lesion. The compounds of the formula (I) inhibit this behavior, with $ED_{50}$ values of 0.05 to 20 mg/kg, preferably up to 5 mg/kg.

The compounds of the formula (I) furthermore greatly inhibit intacranial autostimulation in rats ($ED_{50}$ values of 0.01 to 10 mg/kg, preferably up to 5 mg/kg). In this experiment, rats which have had electrodes implanted in their brain can stimulate themselves by pressing buttons. The dose of the compounds which reduces the number of presses on the button by 50% is determined.

The compounds have little or no cataleptogenic action, ie. they cause cataleptic rigidity in rats only in high doses (>30 mg/kg). In addition, up to high dosages of the compounds (>10 mg/kg intraperitoneal to mice) cause no blocking or only slight blocking of $\alpha$- or $\beta$-adrenergic receptors, ie. the compounds do not have a sympatholytic action.

The abovementioned pharmacological actions are distinctly superior to those of known neuroleptic drugs. Thus, for example, the ratio of effective dose to cataleptogenic dose is 1:20 to 1:180, depending on the test method. For conventional butyrophenone derivatives, such as haloperidol and phenothiazines, such as chlorpromazine, this ratio is 1:4 to 1:8 (P. A. J. Janssen and W. F. M. van Bever in G. Stille, H. Hoffmeister (editors) Psychotropic Agents, Volume I, Springer 1980). When the compounds are used, the cataleptogenic actions lead to undesirable extrapyramidal disorders. In addition, the known neuroleptic drugs frequently have an $\alpha$-sympatholytic side-effect which, inter alia, leads to undesirable lowering of the blood pressure.

The compounds according to the invention and their pharmacologically acceptable salts are effective within a wide dosage range. The level of dosage administered depends on the nature of the desired treatment, of the mode of administration, and on the condition, type and size of the mammal to be treated. In the case of oral dosage, satisfactory results are achieved with doses of 0.01 to 100 mg, preferably up to 10 mg, of a compound of the formula I per kg of animal body weight. In humans, the daily dose varies from 10 mg to 800 mg, preferably from 20 to 500 mg, it being possible to administer individual doses of 5 to 200 mg, preferably one to three times daily. For intravenous and intramuscular administration, the dose is 1 to 300 mg, preferably 5 to 150 mg, daily.

The compounds of the present invention which can be used pharmacologically and their salts can be used for the preparation of pharmaceutical products which contain an effective amount of the active substance together with excipients which are suitable for enteral or parenteral administration. Tablets or gelatin capsules which contain the active compound together with diluents, for example lactose, dextrose, sucrose, mannitol, sorbitol, cellulose and/or glycine, and lubricants, for example siliceous earth, talc or stearic acid or salts thereof, such as magnesium or calcium stearate, and/or polyethylene glycol, are preferably used. Tablets also contain binders, for example magnesium aluminum silicate, starch paste, gelatin, tragacanth, methylcellulose, sodium carboxymethylcellulose and/or polyvinylpyrrolidone, and, if required, colorants, flavor substances or sweeteners. Injectable solutions are preferably isotonic aqueous solutions or suspensions, which may be sterilized and can contain auxiliaries such as preservatives, stabilizers, wetting agents and/or emulsifying agents, solubilizing agents, salts for regulating the osmotic pressure and/or buffer substances. The pharmaceutical products according to the invention, which, if desired, can also contain other pharmacologically valuable substances, are prepared in a manner which is known per se, for example by means of conventional mixing, granulating or tablet-coating processes, and contain about 0.1% to about 75%, preferably about 1% to about 50%, of the active compound.

The examples which follow are intended to illustrate the invention. Percentages are by weight, unless otherwise indicated.

EXAMPLE 1

1-[(Benzo-1,4-dioxan-2-yl)-methyl]-4-(5-chlorobenzimidazol-2-on-1-yl)-piperidine hydrochloride 1.1 1-Carbethoxy-4-(2-nitro-4-chloroanilino)-piperidine A mixture of 0.25 mole of ethyl 4-amino-1-piperidinecarboxylate, 0.3 mole of 1,4-dichloro-2-nitrobenzene, 0.3 mole of sodium carbonate, 0.2 g of potassium iodide and 160 ml of cyclohexanol was stirred at 150° C. for 40 hours. After the mixture had been cooled, toluene and water were added and the organic layer was separated off, washed three times with water, dried and evaporated. The oily residue was dissolved in hot diisopropyl ether and the solution was stirred under reflux with active charcoal, filtered and left to crystallize. Melting point: 116° C.

1.2

1-Carbethoxy-4-(2-amino-4-chloroanilino)-piperidine

A solution of 59 g of 1-carbethoxy-4-(2-nitro-4-chloroanilino)-piperidine in 270 ml of tetrahydrofuran and 96 ml of absolute ethanol was hydrogenated under normal pressure and at room temperature, using 15 g of Raney nickel as a catalyst. When the uptake of hydrogen had ended, the mixture was filtered and the filtrate was evaporated. Melting point: 150° C.

1.3

1-Carbethoxy-4-(5-chlorobenzimidazol-2-on-1-yl)piperidine

A mixture of 24.7 g of 1-carbethoxy-4-(2-amino-4-chloroanilino)-piperidine and 7.2 g of urea was heated to 160°–180° C. for 3.5 hours. The melt was taken up in 250 ml of toluene and heated, while stirring, until everything had dissolved. The solution was clarified with active charcoal, filtered and concentrated to 50 ml. The product was precipitated with diisopropyl ether. Melting point: 160° C.

1.4 4-(5-Chlorobenzimidazol-2-on-1-yl)-piperidine

A mixture of 22.3 g of 1-carbethoxy-4-(5-chlorobenzimidazol-2-on-1-yl)-piperidine, 13 g of 50% strength sodium hydroxide solution and 90 ml of water was boiled under reflux for 24 hours. After the mixture had been cooled, the solution was stirred with 8.5 g of ammonium chloride for 30 minutes and extracted with chloroform, and the undissolved material was filtered off and discarded. The chloroform solution was dried and evaporated. The product crystallized, and has a melting point of 220° C.

The following starting materials were prepared from the correspondingly substituted o-chloro-nitrobenzenes analogously to the instructions in Example 1.1 to 1.4:

4-(6-chlorobenzimidazol-2-on-1-yl)-piperidine, melting point: 130° C. (decomposition)
4-(7-chlorobenzimidazol-2-on-1-yl)-piperidine, melting point: 246° C.
4-(5,6-dichlorobenzimidazol-2-on-1-yl)-piperidine, melting point: 202°–203° C.
4-(5-methylbenzimidazol-2-on-1-yl)-piperidine, melting point: 196°–197° C.
4-(5-methoxybenzimidazol-2-on-1-yl)-piperidine, melting point: 117° C. (decomposition)
4-(5,6-dimethylbenzimidazol-2-on-1-yl)-piperidine
4-(6-methylbenzimidazol-2-on-1-yl)-piperidine
4-(benzimidazol-2-on-1-yl)-piperidine
4-(6-chloro-7-methylbenzimidazol-2-on-1-yl)-piperidine, melting point: 174°–176° C. (decomposition)
4-(5-trifluoromethylbenzimidazol-2-on-1-yl)-piperidine, melting point: >260° C.
4-(5-fluorobenzimidazol-2-on-1-yl)-piperidine, melting point: 159° C.
4-(5-bromobenzimidazol-2-on-1-yl)-piperidine
4-(5-formylbenzimidazol-2-on-1-yl)-piperidine

1.5 2-Hydroxymethyl-1,4-benzodioxane 0.5 mole of pyrocatechol were stirred vigorously with 1.5 moles of epichlorohydrin and 1 mole of 10% strength aqueous potassium hydroxide solution at 100° C. After the mixture had been cooled, it was extracted with ether, the ether extract was washed with dilute potassium hydroxide solution and water, dried and evaporated and the product was recrystallized from ethanol. Melting point: 87°–90° C.

1.6 2-(p-Toluenesulfonyloxymethyl)-1,4-benzodioxane 0.35 mole of 1-hydroxymethyl-1,4-benzodioxane were dissolved in 200 ml of anhydrous pyridine, and 0.38 mole of p-toluenesulfonyl chloride was added. After 16 hours at room temperature, the mixture was acidified with ice-cold dilute hydrochloric acid and extracted with ether. The mixture was dried and concentrated and the product was recrystallized. Melting point: 79° C.

The following compounds were prepared analogously to the above instructions:

2-(p-toluenesulfonyloxymethyl)-5-methyl-1,4-benzodioxane, melting point: 80°–81° C.
2-(p-toluenesulfonyloxymethyl)-8-methyl-1,4-benzodioxane, melting point: 84° C.
2-(p-toluenesulfonyloxymethyl)-5,7-dimethyl-1,4-benzodioxane, oil
2-(p-toluenesulfonyloxymethyl)-6-fluoro-1,4-benzodioxane, oil
2-(p-toluenesulfonyloxymethyl)-7-fluoro-1,4-benzodioxane melting point: 87°–89° C.
2-(p-toluenesulfonyloxymethyl)-5,8-dimethyl-1,4-benzodioxane, melting point: 84°–85° C.
2-(p-toluenesulfonyloxymethyl)-6,7-dimethyl-1,4-benzodioxane, melting point: 93.5°–95° C.
2-(p-toluenesulfonyloxymethyl)-6-acetyl-1,4-benzodioxane, melting point: 72°–75° C.
2-(p-toluenesulfonyloxymethyl)-5-chloro-1,4-benzodioxane, melting point: 83°–84° C.
2-(p-toluenesulfonyloxymethyl)-6-nitro-1,4-benzodioxane, melting point: 119°–122° C.
2-(p-toluenesulfonyloxymethyl)-8-nitro-1,4-benzodioxane, melting point: 96°–98° C.

1.7 2-Chloromethyl-1,4-benzodioxane 0.42 mole of 2-hydroxymethyl-1,4-benzodioxane, 0.42 mole of thionyl chloride and 600 ml of dry pyridine were heated at 100° C. for 3 hours. After the mixture had been cooled, ice-cold dilute hydrochloric acid was added and the mixture was extracted with ether. After drying, the solvent was removed and the residue was distilled in vacuo. Boiling point: 80° C. (0.9 mbar).

The following compounds were likewise synthesized according to these instructions:

2-chloromethyl-6-methyl-1,4-benzodioxane, boiling point: 86°–100° C. (0.2 mbar)
2-chloromethyl-7-methyl-1,4-benzodioxane, boiling point: 96°–102° C. (0.5 mbar)
2-chloromethyl-8-methyl-1,4-benzodioxane, boiling point: 91°–92° C. (0.9 mbar)
2-chloromethyl-7-chloro-1,4-benzodioxane, boiling point: 95°–96° C. (0.4 mbar)

1.8 2-Bromomethyl-1,4-benzodioxane 0.11 mole of phosphorus tribromide in 500 ml of tetrachloroethane was slowly added to 0.3 mole of 2-hydroxymethyl-1,4-benzodioxane and the mixture was warmed at 80°–90° C. for 2 hours. After the mixture had been cooled, it was poured into water, the organic layer was separated off, washed with dilute sodium hydroxide solution and water, dried and concentrated and the residue was distilled. Boiling point: 102°–103° C. (1.3 mbar).

The following compound was also prepared according to these instructions:

2-bromomethyl-6,7-dichloro-1,4-benzodioxane, boiling point: 124°–127° C. (0.3 mbar)

1.9

1-[(Benzo-1,4-dioxan-2-yl)-methyl]-4-(5-chlorobenzimidazol-2-on-1-yl)-piperidine hydrochloride 2.3 g of 2-bromomethyl-1,4-benzodioxane, 2.2 g of 4-(5-chlorobenzimidazol-2-on-1-yl)-piperidine, 1.4 ml of triethylamine and 0.3 g of sodium iodide were stirred in 25 ml of dry dimethylformamide at room temperature for 60 hours and the mixture was then poured onto water; diisopropyl ether was added and the mixture was stirred vigorously for 2 hours. The product which had precipitated was filtered off with suction, washed with water and diisopropyl ether and dried; the free base thus obtained has a melting point of 226°–228° C.

NMR: 11.0 s (1H); 7.3–6.6 m (7H); 4.5–3.6 m (4H); and 3.3–1.5 m (10H)

IR: 1685 cm$^{-1}$

Hydrochloride: The base was dissolved in methylene chloride/methanol. 3 ml of 2.5N ethanolic HCl were added, the mixture was concentrated to dryness and the residue was taken up in acetone twice and the mixture concentrated to dryness each time; colorless powder of melting point 196°–200° C. (decomposition).

Analysis calculated: C 57.8; H 5.3; found: C 57.7; H 5.7

EXAMPLE 2

1-[(Benzo-1,4-dioxan-2-yl)-methyl]-4-(benzimidazol-2-on-1-yl)-piperidine hydrochloride 0.018 mole of 2-(p-toluenesulfonyloxymethyl)-1,4-benzodioxane, 0.018 mole of 4-(benzimidazol-2-on-1-yl)-piperidine, 3.6 g of potassium carbonate and 60 ml of absolute dimethylformamide were heated at 170° C. for 2 hours. After the mixture had been cooled, it was poured onto water and the precipitate was filtered off with suction, washed with water and dried; the free base thus obtained has a melting point of 183°–184° C.

NMR: 10.3 s (1H); 7.3–6.8 m (8H); 4.6–4.0 m (4H); and 3.3–1.5 m (10H)
IR: 1690 cm$^{-1}$ Hydrochloride: colorless powder, melting point: 193°–195° C.

The following compounds were prepared analogously to the instructions given in Examples 1.9 and 2, using appropriate amounts of the starting materials in question:

EXAMPLE 3

1-[(5-Methyl-benzo-1,4-dioxan-2-yl)-methyl]-4-(5-chlorobenzimidazol-2-on-1-yl)-piperidine NMR: 10.5 s (1H); 7.3–6.8 m (6H); 4.6–4.0 m (4H); and 3.3–1.5 m+s (13H).
IR: 1685 cm$^{-1}$

EXAMPLE 4

1-[(5-Methyl-benzo-1,4-dioxan-2-yl)-methyl]-4-(6-chlorobenzimidazol-2-on-1-yl)-piperidine NMR: 10.4 s (1H); 7.4–6.7 m (6H); 4.6–4.0 m (4H); and 3.3–1.5 m+s (13H)
IR: 1690 cm$^{-1}$

EXAMPLE 5

1-[(5-Methyl-benzo-1,4-dioxan-2-yl)-methyl]-4-(benzimidazol-2-on-1-yl)-piperidine NMR: 10.8 s (1H); 7.3–6.7 m (7H); 4.6–4.1 m (4H); and 3.3–1.5 m+s (13H)
IR: 1689 cm$^{-1}$

EXAMPLE 6

1-[(6-Methyl-benzo-1,4-dioxan-2-yl)-methyl]-4-(benzimidazol-2-on-1-yl)-piperidine NMR: 10.4 s (1H); 7.4–6.8 m (6H); 4.6–3.9 m (4H); and 3.3–1.5 m+s (13H);
IR: 1685 cm$^{-1}$

EXAMPLE 7

1-[(6-Methyl-benzo-1,4-dioxan-2-yl)-methyl]-4-(5-chlorobenzimidazol-2-on-1-yl)-piperidine Free base: melting point: 164°–166° C.
NMR: 10.8 s (1H); 7.4–6.6 m (6H); 4.6–3.9 m (4H); and 3.3–1.5 m+s (13H)
IR: 1691 cm$^{-1}$ Hydrochloride: melting point: 224°–226° C. (decomposition).

EXAMPLE 8

1-[(6-Methyl-benzo-1,4-dioxan-2-yl)-methyl]-4-(7-chlorobenzimidazol-2-on-1-yl)-piperidine NMR: 10.6 s (1H); 7.4–6.6 m (6H); 4.5–3.9 m (4H); and 3.3–1.5 m+s (13H)
IR: 1694 cm$^{-1}$

EXAMPLE 9

1-[(7-Methyl-benzo-1,4-dioxan-2-yl)-methyl]-4-(5-chlorobenzimidazol-2-on-1-yl)-piperidine NMR: 10.6 s (1H); 7.4–6.6 m (6H); 4.5–3.9 m (4H); and 3.3–1.5 m+s (13H)
IR: 1685 cm$^{-1}$

EXAMPLE 10

1-[(7-Methyl-benzo-1,4-dioxan-2-yl)-methyl]-4-(7-chlorobenzimidazol-2-on-1-yl)-piperidine NMR: 10.8 s (1H); 7.3–6.6 m (6H); 4.5–3.9 m (4H); and 3.3–1.5 m+s (13H)
IR: 1688 cm$^{-1}$

EXAMPLE 11

1-[(6-Acetyl-benzo-1,4-dioxan-2-yl)-methyl]-4-(5-chlorobenzimidazol-2-on-1-yl)-piperidine NMR: 10.4 s (1H); 7.7–6.6 m (6H); 4.5–3.9 m (4H); 3.3–1.5 m+s (13H); and 2.1 s (3H)
IR: 1698 and 1685 cm$^{-1}$

EXAMPLE 12

1-[(6-Acetyl-benzo-1,4-dioxan-2-yl)-methyl]-4-(benzimidazol-2-on-1-yl)-piperidine NMR: 10.6 s (1H), 7.7–6.7 m (7H); 4.5–3.9 m (4H); 3.3–1.4 m+s (13H); and 2.1 s (3H)
IR: 1698 and 1690 cm$^{-1}$

EXAMPLE 13

1-[(5,7-Dimethyl-benzo-1,4-dioxan-2-yl)-methyl]-4-(benzimidazol-2-on-1-yl)-piperidine NMR: 10.8 s (1H); 7.3–6.5 m (6H); 4.5–3.9 m (4H); 3.3–1.4 m+2s (16H)
IR: 1695 cm$^{-1}$

EXAMPLE 14

1-[(5,7-Dimethyl-benzo-1,4-dioxan-2-yl)-methyl]-4-(5-chloro-benzimidazol-2-on-1-yl)-piperidine NMR: 10.7 s (1H); 7.2–6.5 m (5H); 4.5–4.0 m (4H); and 3.3–1.5 m+2s (16H);
IR: 1688 cm$^{-1}$

EXAMPLE 15

1-[(5,8-Dimethyl-benzo-1,4-dioxan-2-yl)-methyl]-4-(5-chlorobenzimidazol-2-on-1-yl)-piperidine NMR: 11.0 s (1H); 7.3–6.5 m (5H); 4.5–4.0 m (4H); and 3.3–1.5 m+2s (16H) IR: 1684 cm$^{-1}$

EXAMPLE 16

1-[(5,8-Dimethyl-benzo-1,4-dioxan-2-yl)-methyl]-4-(benzimidazol-2-on-1-yl)-piperidine NMR: 10.9 s (1H); 7.3–6.5 m (6H); 4.6–4.0 m (4H); and 3.3–1.5 m+2s (16H)
IR: 1690 cm$^{-1}$

EXAMPLE 17

1-[(6,7-Dimethyl-benzo-1,4-dioxan-2-yl)-methyl]-4-(benzimidazol-2-on-1-yl)-piperidine NMR: 10.7 s (1H); 7.3–6.5 m (6H); 4.6–4.0 m (4H); and 3.3–1.5 m+2s (16H)
IR: 1687 cm$^{-1}$

EXAMPLE 18

1-[(6,7-Dimethyl-benzo-1,4-dioxan-2-yl)-methyl]-4-(5-chlorobenzimidazol-2-on-1-yl)-piperidine NMR: 10.8 s (1H); 7.4–6.6 m (5H); 4.5–3.9 m (4H); and 3.3–1.4 m+2s (16H)
IR: 1683 cm$^{-1}$

EXAMPLE 19

1-[(5-Chloro-benzo-1,4-dioxan-2-yl)-methyl]-4-(5-chlorobenzimidazol-2-on-1-yl)-piperidine NMR: 10.9 s (1H); 7.4–6.7 m (6H); 4.5–3.9 m (4H); and 3.4–1.5 (10H)
IR: 1684 cm$^{-1}$

EXAMPLE 20

1-[(5-Chloro-benzo-1,4-dioxan-2-yl)-methyl]-4-(benzimidazol-2-on-1-yl)-piperidine NMR: 11.2 s (1H); 7.5–6.7 m (7H); 4.5–3.9 m (4H); and 3.4–1.4 m (10H)
IR: 1679 cm$^{-1}$

EXAMPLE 21

1-[(7-Chloro-benzo-1,4-dioxan-2-yl)-methyl]-4-(5-chlorobenzimidazol-2-on-1-yl)-piperidine Free base: melting point: 184°–189° C.
NMR: 11.0 s (1H); 7.4–6.6 m (6H); 4.5–3.9 m (4H); and 3.5–1.5 m (10H)
IR: 1683 cm$^{-1}$
Hydrochloride: melting point: >180° C. (decomposition)

EXAMPLE 22

1-[(7-Chloro-benzo-1,4-dioxan-2-yl)-methyl]-4-(5-methylbenzimidazol-2-on-1-yl)-piperidine Free base: melting point: 187° C.
NMR: 10.9 s (1H); 7.4–6.7 m (6H); 4.5–3.9 m (4H); and 3.5–1.5 m+s (13H)
IR: 1686 cm$^{-1}$
Hydrochloride: melting point: 245° C. (decomposition)

EXAMPLE 23

1-[(7-Chloro-benzo-1,4-dioxan-2-yl)-methyl]-4-(benzimidazol-2-on-1-yl)-piperidine NMR: 10.9 s (1H); 7.4–6.7 m (7H); 4.5–3.9 m (4H); and 3.5–1.5 m (10H)
IR: 1688 cm$^{-1}$

EXAMPLE 24

1-[(6,7-Dichloro-benzo-1,4-dioxan-2-yl)-methyl]-4-(5-chlorobenzimidazol-2-on-1-yl)-piperidine Free base: melting point 238°–240° C.
NMR: 10.7 s (1H); 7.4–6.7 m (5H); 4.5–3.9 m (4H); and 3.5–1.5 m (10H)
IR: 1682 cm$^{-1}$
Hydrochloride: melting point: 289°–290° C.

EXAMPLE 25

1-[(6,7-Dichloro-benzo-1,4-dioxan-2-yl)-methyl]-4-(benzimidazol-2-on-1-yl)-piperidine NMR: 10.95 s (1H); 7.4–6.7 m (6H); 4.5–3.9 m (4H); and 3.5–1.5 m (10H)
IR: 1690 cm$^{-1}$

EXAMPLE 26

1-[(6,7-Dichloro-benzo-1,4-dioxan-2-yl)-methyl)]-4-(5-methylbenzimidazol-2-on-1-yl)-piperidine NMR: 11.1 s (1H); 7.4–6.7 m (5H); 4.5–3.9 m (4H); and 3.6–1.4 m+s (13H)
IR: 1690 cm$^{-1}$

EXAMPLE 27

1-[(6-Nitro-benzo-1,4-dioxan-2-yl)-methyl)]-4-(5-chlorobenzimidazol-2-on-1-yl)-piperidine NMR: 11.2 s (1H); 8.0–6.7 m (6H); 4.5–3.9 m (4H); and 3.5–1.5 m (10H)
IR: 1688 and 1530 cm$^{-1}$

EXAMPLE 28

1-[(6-Nitro-benzo-1,4-dioxan-2-yl)-methyl)]-4-(benzimidazol-2-on-1-yl)-piperidine NMR: 11.0 s (1H); 8.0–6.8 m (7H); 4.5–3.9 m (4H); and 3.5–1.4 m (10H)
IR: 1692 cm$^{-1}$

EXAMPLE 29

1-[(7-Nitro-benzo-1,4-dioxan-2-yl)-methyl]-4-(5-chlorobenzimidazol-2-on-1-yl)-piperidine NMR: 10.7 s (1H); 8.0–6.9 m (6H); 4.5–3.9 m (6H); 4.5–3.9 m (4H); and 3.5–1.6 m (10H)
IR: 1688 cm$^{-1}$

EXAMPLE 30

1-[(7-Nitro-benzo-1,4-dioxan-2-yl)-methyl]-4-(benzimidazol-2-on-1-yl)-piperidine NMR: 10.8 s (1H); 8.0–6.9 m (7H); 4.5–3.9 m (4H); and 3.5–1.5 m (10H)
IR: 1687 and 1530 cm$^{-1}$

EXAMPLE 31

1-[(Benzo-1,4-dioxan-2-yl)-methyl]-4-(5-chlorobenzimidazole-2-thion-1-yl)-piperidine 31.1 4-(5-Chlorobenzimidazole-2-thion-1-yl)-piperidine 6 g of 1-carbethoxy-4-(2-amino-4-chloroanilino)-piperidine (1.2) were boiled under reflux, with stirring, in 35 ml of carbon disulfide and 30 ml of ethanol for 24 hours. After the mixture had been evaporated, the residue was crystallized from ethanol. The product thus obtained was boiled under reflux with 50 ml of 10% strength sodium hydroxide solution for 24 hours. After the mixture had been cooled, the solution was neutralized with ammonium chloride and extracted with chloroform. The organic layer was dried and concentrated. The product thus obtained has a melting point of 282°–284° C. The following compounds were also prepared according to the same instructions:

4-(benzimidazole-2-thion-1-yl)-piperidine, melting point: 250°–251° C.

4-(5-trifluoromethyl-benzimidazole-2-thion-1-yl)-piperidine

31.2

1-[(Benzo-1,4-dioxan-2-yl)-methyl]-4-(5-chlorobenzimidazole-2-thion-1-yl)-piperidine 2.3 g of 2-bromomethyl-1,4-benzodioxane, 2.35 g of 4-(5-chlorobenzimidazole-2-thion-1-yl)-piperidine, 1.4 ml of triethylamine and 0.3 g of sodium iodide were warmed at 60° C. in 25 ml of anhydrous dimethylformamide for 60 hours, and the mixture was then poured onto ice-water. The precipitate which had separated out was filtered off with suction, washed with water and dried.

NMR: 9.2 s (1H); 7.3–6.5 m (7H); 4.5–3.9 m (4H); and 3.5–1.5 m (10H)
Hydrochloride: melting point: 263°–265° C. (decomposition)

The following compounds were prepared analogously, according to the instructions, using the appropriate amount of starting materials:

EXAMPLE 32

1-[(Benzo-1,4-dioxan-2-yl)-methyl]-4-(benzimidazole-2-thion-1-yl)-piperidine, hydrochloride: melting point: 207°–211° C. (decomposition)

NMR: 9.0 s (1H); 7.3–6.5 m (8H); 4.5–3.9 m (4H); and 3.5–1.5 m (10H)

EXAMPLE 33

1-[(5-Methyl-benzo-1,4-dioxan-2-yl)-methyl]-4-(5-chlorobenzimidazol-2-thion-1-yl)-piperidine NMR: 9.3 s (1H); 7.3–6.4 m (6H); 4.5–3.9 m (4H); and 3.5–1.5 m+s (13H)

EXAMPLE 34

1-[(5-Methyl-benzo-1,4-dioxan-2-yl)-methyl]-4-(benzimidazole-2-thion-1-yl)-piperidine NMR: 9.1 s (1H); 7.3–6.5 m (7H); 4.5–3.9 m (4H); and 3.5–1.5 m+s (13H)

EXAMPLE 35

1-[(5,8-Dimethyl-benzo-1,4-dioxan-2-yl)-methyl]-4-(5-chlorobenzimidazole-2-thion-1-yl)-piperidine NMR: 9.4 s (1H); 7.3–6.5 m (5H); 4.5–3.9 m (4H); and 3.5–1.5 m+2s (16H)

EXAMPLE 36

1-[(5,8-Dimethyl-benzo-1,4-dioxan-2-yl)-methyl]-4-(5-trifluoromethyl-benzimidazole-2-thion-1-yl)-piperidine NMR: 9.6 s (1H); 7.7–6.5 m (5H); 4.5–3.9 m (4H); and 3.5–1.5 m+2s (16H)

EXAMPLE 37

1-[(5-Chloro-benzo-1,4-dioxan-2-yl)-methyl]-4-(5-chlorobenzimidazole-2-thion-1-yl)-piperidine NMR: 9.2 s (1H); 7.3–6.5 m (6H); 4.5–3.9 m (4H); and 3.5–1.5 m (10H)

EXAMPLE 38

1-[(5-Chloro-benzo-1,4-dioxan-2-yl)-methyl]-4-(benzimidazole-2-thion-1-yl)-piperidine NMR: 9.2 s (1H); 7.3–6.5 m (7H); 4.5–3.9 m (4H); and 3.5–1.5 m (10H)

EXAMPLE 39

1-[(6-Nitro-benzo-1,4-dioxan-2-yl)-methyl]-4-(5-chlorobenzimidazole-2-thion-1-yl)-piperidine NMR: 9.2 s (1H); 8.2–6.5 m (6H); 4.5–3.9 m (4H); and 3.5–1.5 m (10H)

EXAMPLE 40

1-[(6-Nitro-benzo-1,4-dioxan-2-yl)-methyl]-4-(benzimidazole-2-thion-1-yl)-piperidine NMR: 9.2 s (1H); 8.2–6.5 m (7H); 4.5–3.3 m (4H); and 3.5–1.5 m (10H)

EXAMPLE 41

1-[(Benzo-1,4-dioxan-2-yl)-methyl]-4-(6-chlorobenzimidazol-2-on-1-yl)-piperidine

41.1 4-(5-Chloro-2-nitroanilino)-piperidine hydrobromide 30 g of 1-carbethoxy-4-(5-chloro-2-nitroanilino)-piperidine in 400 ml of 48% strength hydrobromic acid were boiled under reflux, with stirring, for 4 hours. After the mixture had been cooled, the precipitate which had formed was filtered off with suction and washed with water and petroleum ether. The product was obtained as a light beige powder.

41.2 1-[(Benzo-1,4-dioxan-2-yl)-methyl]-4-(5-chloro-2-nitroanilino)-piperidine 11.5 g of 2-bromomethyl-1,4-benzodioxane, 20.4 g of 4-(5-chloro-2-nitroanilino)-piperidine hydrobromide, 20 g of potassium carbonate and 0.5 g of potassium iodide were dissolved in 120 ml of methyl isopropyl ketone and the solution was heated under reflux for 24 hours. After the mixture had been cooled, water was added and the organic phase was separated off, dried and concentrated.

41.3 1-[(Benzo-1,4-dioxan-2-yl)-methyl]-4-(5-chloro-2-aminoanilino)-piperidine 20 g of 1-[(benzo-1,4-dioxan-2-yl)-methyl]-4-(5-chloro-2-nitroanilino)-piperidine were hydrogenated under normal pressure and at room temperature, using 4 g of Raney nickel as a catalyst in 200 ml of ethanol. When the uptake of hydrogen had ended, the mixture was filtered, the material on the filter was rinsed with ethanol and the filtrate was concentrated.

41.4 1-[(Benzo-1,4-dioxan-2-yl)-methyl]-4-(6-chlorobenzimidazol-2-on-1-yl)-piperidine A solution of 4.8 g of potassium cyanate in 10 ml of water was added to 14.5 g of 1-[(benzo-1,4-dioxan-2-yl)-methyl]-4-(5-chloro-2-aminoanilino)-piperidine in 5 ml of 10% strength hydrochloric acid and 40 ml of water, whilst cooling and stirring. When the addition had ended, the mixture was stirred at room temperature for 1 hour and then under reflux for 24 hours. After the mixture had been cooled, it was extracted with chloroform. The extract was washed with 5% strength hydrochloric acid, dried and filtered and the filtrate was concentrated.

Melting point: 232°–234° C.
NMR: 10.5 s (1H); 7.3–6.8 m (7H); 4.6–4.0 m (4H); and 3.3–1.5 m (10H)
IR: 1686 cm$^{-1}$ Hydrochloride: melting point: 230°–232° C. (decomposition)

The following compounds were prepared in the same manner from the corresponding starting substances:

EXAMPLE 42

1-[(Benzo-1,4-dioxan-2-yl)-methyl]-4-(7-chlorobenzimidazol-2-on-1-yl)-piperidine Free base: melting point: 171°–174° C.
NMR: 10.5 s (1H); 7.3–6.8 m (7H); 4.6–4.0 m (4H); and 3.3–1.5 m (10H)
IR: 1685 cm$^{-1}$ Hydrochloride: melting point: 236° C.

EXAMPLE 43

1-[(Benzo-1,4-dioxan-2-yl)-methyl]-4-(5,6-dichlorobenzimidazol-2-on-1-yl)-piperidine Free base: melting point: 207°–211° C.
NMR: 10.6 s (1H); 7.4–6.8 m (6H); 4.6–4.0 m (4H); and 3.3–1.5 m (10H)
IR: 1681 cm$^{-1}$
Hydrochloride: melting point: 218°–222° C.

EXAMPLE 44

1-[(Benzo-1,4-dioxan-2-yl)-methyl]-4-(5-methylbenzimidazol-2-on-1-yl)-piperidine Free base: melting point: 209°–215° C.
NMR: 10.3 s (1H); 7.4–6.8 m (7H); 4.6–4.0 m (4H); and 3.3–1.4 m+s (13H)
IR: 1691 cm$^{-1}$
Hydrochloride: melting point: 212°–214° C.

EXAMPLE 45

1-[(Benzo-1,4-dioxan-2-yl)-methyl]-4-(5-trifluoromethylbenzimidazol-2-on-1-yl)-piperidine Free base: melting point: 104° C. (decomposition)
NMR: 10.8 s (1H); 8.0–6.8 m (7H); 4.6–4.0 m (4H); and 3.4–1.6 m (10H)
IR: 1680 cm$^{-1}$
Hydrochloride: melting point: 243°–247° C.

EXAMPLE 46

1-[(Benzo-1,4-dioxan-2-yl)-methyl]-4-(5,6-dimethylbenzimidazol-2-on-1-yl)-piperidine NMR: 10.4 s (1H); 7.1–6.5 m (6H); 4.6–4.0 m (4H); and 3.5–1.5 m+s (16H)
IR: 1678 cm$^{-1}$

EXAMPLE 47

1-[(Benzo-1,4-dioxan-2-yl)-methyl]-4-(6-methylbenzimidazol-2-on-1-yl)-piperidine NMR: 10.8 s (1H); 7.2–6.6 m (7H); 4.7–4.0 m (4H); and 3.4–1.3 m+s (13H)
IR: 1682 cm$^{-1}$

EXAMPLE 48

1-[(5-Methyl-benzo-1,4-dioxan-2-yl)-methyl]-4-(5-methylbenzimidazol-2-on-1-yl)-piperidine NMR: 10.9 s (1H); 7.2–6.5 m (6H); 4.7–4.0 m (4H); and 3.4–1.3 m+s (16H)

EXAMPLE 49:

1-[(5-Methyl-benzo-1,4-dioxan-2-yl)-methyl]-4-(5-trifluoromethyl-benzimidazol-2-on-1-yl)-piperidine NMR: 10.7 s (1H); 7.8–6.5 m (6H); 4.7–4.0 (4H); and 3.3–1.3 m+s (13H)
IR: 1680 cm$^{-1}$

EXAMPLE 50

1-[(6-Methyl-benzo-1,4-dioxan-2-yl)-methyl]-4-(5,6-dichlorobenzimidazol-2-on-1-yl)-piperidine NMR: 10.9 s (1H); 7.4–6.5 m (5H); 4.7–4.0 m (4H); and 3.3–1.3 m+s (13H)
IR: 1678 cm$^{-1}$

EXAMPLE 51

1-[(6-Methyl-benzo-1,4-dioxan-2-yl)-methyl]-4-(6-methylbenzimidazol-2-on-1-yl)-piperidine NMR: 10.8 s (1H); 7.2–6.5 m (6H); 4.6–4.0 m (4H); and 3.5–1.4 m+2s (16H)
IR: 1688 cm$^{-1}$

EXAMPLE 52

1-[(7-Methyl-benzo-1,4-dioxan-2-yl)-methyl]-4-(benzimidazol-2-on-1-yl)-piperidine NMR: 11.0 s (1H); 7.3–6.6 m (7H); 4.6–4.0 m (4H); and 3.6–1.5 m+s (13H)
IR: 1690 cm$^{-1}$

EXAMPLE 53

1-[(7-Methyl-benzo-1,4-dioxan-2-yl)-methyl]-4-(5-trifluoromethyl-benzimidazol-2-on-1-yl)-piperidine NMR: 11.1 s (1H); 7.9–6.6 m (6H); 4.6–4.0 m (4H); and 3.8–1.4 m+s (13H)
IR: 1692 cm$^{-1}$

EXAMPLE 54

1-[(5,7-Dimethyl-benzo-1,4-dioxan-2-yl)-methyl]-4-(5,6-dimethyl-benzimidazol-2-on-1-yl)-piperidine NMR: 10.9 s (1H); 7.1–6.6 m (4H); 4.6–4.0 m (4H); and 3.6–1.3 m+4s (22H)
IR: 1685 cm$^{-1}$

EXAMPLE 55

1-[(5,8-Dimethyl-benzo-1,4-dioxan-2-yl)-methyl]-4-(5-trifluoromethyl-benzimidazol-2-on-1-yl)-piperidine NMR: 10.7 s (1H); 7.9–6.6 m (5H); 4.6–4.0 m (4H); and 3.5–1.4 m+2s (16H)
IR: 1690 cm$^{-1}$

EXAMPLE 56

1-[(6,7-Dimethyl-benzo-1,4-dioxan-2-yl)-methyl]-4-(5-methylbenzimidazol-2-on-1-yl)-piperidine NMR: 10.8 s (1H); 7.3–6.6 m (5H); 4.6–4.0 m (4H); and 3.5–1.4 m+3s (19H)
IR: 1688 cm$^{-1}$

EXAMPLE 57

1-[(5-Chloro-benzo-1,4-dioxan-2-yl)-methyl]-4-(5-trifluoromethyl-benzimidazol-2-on-1-yl)-piperidine

EXAMPLE 58

1-[(7-Chloro-benzo-1,4-dioxan-2-yl)-methyl]-4-(5,6-dichlorobenzimidazol-2-on-1-yl)-piperidine NMR: 10.7 s (1H); 7.3–6.6 m (5H); 4.5–3.9 m (4H); and 3.5–1.5 m (10H)
IR: 1688 cm$^{-1}$

EXAMPLE 59

1-[(6,7-Dichloro-benzo-1,4-dioxan-2-yl)-methyl]-4-(5-trifluoromethyl-benzimidazol-2-on-1-yl)-piperidine NMR: 10.9 s (1H); 7.8–6.6 m (5H); 4.5–3.9 m (4H); and 3.5–1.5 m (10H)
IR: 1685 cm$^{-1}$

EXAMPLE 60

1-[(6-Nitro-benzo-1,4-dioxan-2-yl)-methyl]-4-(5,6-dichlorobenzimidazol-2-on-1-yl)-piperidine NMR: 10.9 s (1H); 8.3–6.7 m (5H); 4.5–3.9 m (4H); and 3.5–1.5 m (10H)

IR: 1685 and 1530 cm$^{-1}$

EXAMPLE 61

1-[(8-Nitro-benzo-1,4-dioxan-2-yl)-methyl]-4-(6-chlorobenzimidazol-2-on-1-yl)-piperidine NMR: 10.6 s (1H); 8.2–6.8 m (6H); 4.5–4.0 m (4H); and 3.5–1.5 m (10H)

IR: 1685 and 1530 cm$^{-1}$

EXAMPLE 62

1-[(8-Nitro-benzo-1,4-dioxan-2-yl)-methyl]-4-(6-methyl-benzimidazol-2-on-1-yl)-piperidine NMR: 10.8 s (1H); 8.3–6.9 m (6H); 4.5–4.0 m (4H); and 3.5–1.5 m+s (13H)

IR: 1685 and 1530 cm$^{-1}$

The following compounds were also prepared analogously to the instructions given in Examples 1,9 and 2, using appropriate amounts of the starting materials in question:

EXAMPLE 63

1-[(Benzo-1,4-dioxan-2-yl)-methyl]-4-(5-fluorobenzimidazol-2-on-1-yl)-piperidine Free base: melting point: 174°–178° C.

NMR: 11.0 s (1H); 7.3–6.5 m (7H); 4.5–3.6 m (4H); and 3.3–1.5 m (10H)

IR: 1688 cm$^{-1}$

Hydrochloride: colorless powder, melting point: 169° C. (decomposition)

EXAMPLE 64

1-[(Benzo-1,4-dioxan-2-yl)-methyl]-4-(5-methoxybenzimidazol-2-on-1-yl)-piperidine Free base: melting point: 177°–181° C.

NMR: 11.0 s (1H); 7.3–6.2 m (7H); 4.5–3.6 m+s (7H); and 3.3–1.5 m (10H)

IR: 1680 cm$^{-1}$

Hydrochloride, melting point: 220°–223° C. (decomposition)

EXAMPLE 65

1-[(Benzo-1,4-dioxan-2-yl)-methyl]-4-(5-bromobenzimidazol-2-on-1-yl)-piperidine

NMR: 10.8 s (1H); 7.4–6.8 m (7H); 4.6–4.0 m (4H); and 3.3–1.5 m (10H)

IR: 1690 cm$^{-1}$

EXAMPLE 66

1-[(Benzo-1,4-dioxan-2-yl)-methyl]-4-(5-formylbenzimidazol-2-on-1-yl)-piperidine NMR: 10.9 s (1H); 10.1 s (1H); 7.8–7.1 m (7H); 4.6–4.0 m (4H); and 3.3–1.5 m (10H)

IR: 1705 and 1690 cm$^{-1}$

EXAMPLE 67

1-[(Benzo-1,4-dioxan-2-yl)-methyl]-4-(6-chloro-7-methyl)-benzimidazol-2-on-1-yl)-piperidine Free base: melting point: 187° C.

NMR: 10.8 s (1H); 7.6–6.8 m (6H); 4.6–4.0 m (4H); 2.3 s (3H); and 3.3–1.5 m (10H)

IR: 1690 cm$^{-1}$

Hydrochloride, melting point: 254°–255° C.

EXAMPLE 68

1-[(5-Methyl-benzo-1,4-dioxan-2-yl)-methyl]-4-(5-fluorobenzimidazol-2-on-1-yl)-piperidine NMR: 10.8 s (1H); 7.3–6.8 m (6H); 4.6–4.0 m (4H); and 3.3–1.5 m+s (13H)

IR: 1685 cm$^{-1}$

EXAMPLE 69

1-[(5-Methyl-benzo-1,4-dioxan-2-yl)-methyl]-4-(5-methoxybenzimidazol-2-on-1-yl)-piperidine NMR: 10.9 s (1H); 7.3–6.4 m (6H); 4.6–4.0 m+s (7H); and 3.3–1.5 m+s (13H)

IR: 1690 cm$^{-1}$

EXAMPLE 70

1-[(6-Methyl-benzo-1,4-dioxan-2-yl)-methyl]-4-(5-methylbenzimidazol-2-on-1-yl)-piperidine NMR: 10.8 s (1H); 7.3–6.4 m (6H); 4.6–4.0 m (4H); and 3.3–1.5 m+2s (16H)

IR: 1685 cm$^{-1}$

EXAMPLE 71

1-[(6-Methyl-benzo-1,4-dioxan-2-yl)-methyl]-4-(5-methoxybenzimidazol-2-on-1-yl)-piperidine NMR: 10.9 s (1H); 7.3–6.2 m (6H); 4.6–4.0 m+s (7H); and 3.3–1.5 m+s (13H)

IR: 1685 cm$^{-1}$

EXAMPLE 72

1-[(6-Methyl-benzo-1,4-dioxan-2-yl)-methyl]-4-(5-fluorobenzimidazol-2-on-1-yl)-piperidine Free base: melting point: 178°–180° C.

NMR: 10.8 s (1H); 7.4–6.8 m (6H); 4.4–3.8 m (4H); and 3.3–1.5 m+s (13H)

IR: 1685 cm$^{-1}$

Hydrochloride, melting point: >170° C. (decomposition)

EXAMPLE 73

1-[(6,7-Dimethyl-benzo-1,4-dioxan-2-yl)-methyl]-4-(5-fluorobenzimidazol-2-on-1-yl)-piperidine NMR: 10.9 s (1H); 7.4–6.8 m (5H); 4.4–3.9 m (4H); and 3.3–1.4 m+2s (16H)

IR: 1685 cm$^{-1}$

EXAMPLE 74

1-[(6,7-Dimethyl-benzo-1,4-dioxan-2-yl)-methyl]-4-(5-methoxybenzimidazol-2-on-1-yl)-piperidine NMR: 10.9 s (1H); 6.9–6.0 m (5H); 4.6–3.9 m+s (7H); and 3.3–1.4 m+2s (16H)

IR: 1690 cm$^{-1}$

EXAMPLE 75

1-[(7-Chloro-benzo-1,4-dioxan-2-yl)-methyl]-4-(5-fluorobenzimidazol-2-on-1-yl)-piperidine Free base, melting point: 152°–154° C.

NMR: 10.9 s (1H); 7.3–6.6 m (6H); 4.6–4.0 m (4H); and 3.5–1.5 m (10H)

IR: 1685 cm$^{-1}$

Hydrochloride, melting point: 233°–236° C. (decomposition)

EXAMPLE 76

1-[(7-Chloro-benzo-1,4-dioxan-2-yl)-methyl]-4-(5-methoxybenzimidazol-2-on-1-yl)-piperidine NMR: 10.9 s (1H); 7.1–6.5 m (6H); 4.6–4.0 m+s (7H); and 3.5–1.5 m (10H)
IR: 1690 cm$^{-1}$

EXAMPLE 77

1-[(6,7-Dichloro-benzo-1,4-dioxan-2-yl)-methyl]-4-(5-methoxybenzimidazol-2-on-1-yl)-piperidine NMR: 11.0 s (1H); 7.3–6.3 m (5H); 4.6–4.0 m+s (7H); and 3.5–1.5 m (10H)
IR: 1690 cm$^{-1}$

EXAMPLE 78

1-[(6,7-Dichloro-benzo-1,4-dioxan-2-yl)-methyl]-4-(5-fluorobenzimidazol-2-on-1-yl)-piperidine Free base, melting point: 199°–201° C.
NMR: 11.0 s (1H); 7.3–6.9 m (5H); 4.6–4.0 m (4H); and 3.5–1.5 m (10H)
IR: 1688 cm$^{-1}$
Hydrochloride, melting point: >240° C. (decomposition)

EXAMPLE 79

1[(6-Fluoro-benzo-1,4-dioxan-2-yl)-methyl]-4-(5-chlorobenzimidazol-2-on-1-yl)-piperidine Free base, melting point: 213°–217° C.
NMR: 10.6 s (1H); 7.3–6.7 m (6H); 4.6–4.0 m (4H); and 3.5–1.5 m (10H)
IR: 1690 cm$^{-1}$
Hydrochloride, melting point: 262°–265° C.

EXAMPLE 80

1-[(7-Fluoro-benzo-1,4-dioxan-2-yl)-methyl]-4-(5-chlorobenzimidazol-2-on-1-yl)-piperidine Free base, melting point: 232°–234° C.
NMR: 10.9 s (1H); 7.3–6.7 m (6H); 4.6–4.0 m (4H); and 3.5–1.5 m (10H)
IR: 1690 cm$^{-1}$
Hydrochloride, melting point: 192°–194° C.

EXAMPLE 81

1[(6-Fluoro-benzo-1,4-dioxan-2-yl)-methyl]-4-(5-fluorobenzimidazol-2-on-1-yl)-piperidine Free base: melting point: 209° C.
NMR: 11.0 s (1H); 7.4–6.7 m (6H); 4.6–4.0 m (4H); and 3.5–1.5 m (10H)
IR: 1690 cm$^{-1}$ Hydrochloride, melting point: 237° C.

EXAMPLE 82

1-[(7-Fluoro-benzo-1,4-dioxan-2-yl)-methyl]-4-(5-fluorobenzimidazol-2-on-1-yl)-piperidine Free base, melting point: 140° C. (decomposition)
NMR: 11.0 s (1H); 7.4–6.7 m (6H); 4.6–4.0 m (4H); and 3.5–1.5 m (10H)
IR: 1685 cm$^{-1}$ Hydrochloride, melting point: 247°–250° C. (decomposition)

EXAMPLE 83

1-[(6-Fluoro-benzo-1,4-dioxan-2-yl)-methyl]-4-(5-methylbenzimidazol-2-on-1-yl)-piperidine NMR: 11.0 s (1H); 7.4–6.6 m (6H); 4.6–4.0 m (4H); and 3.5–1.5 m+s (13H)
IR: 1685 cm$^{-1}$

EXAMPLE 84

1-[(7-Fluoro-benzo-1,4-dioxan-2-yl)-methyl]-4-(5-methylbenzimidazol-2-on-1-yl)-piperidine Free base, melting point: 231° C.
NMR: 11.0 s (1H); 7.4–6.6 m (6H); 4.6–4.0 m (4H); and 3.5–1.5 m+s (13H)
IR: 1685 cm$^{-1}$ Hydrochloride, melting point: 292°–295° C.

EXAMPLE 85

1-[(7-Fluoro-benzo-1,4-dioxan-2-yl)-methyl]-4-(6-chloro-7-methylbenzimidazol-2-on-1-yl)-piperidine Free base, melting point: 201°–203° C.
NMR: 11.0 s (1H), 7.4–6.6 m (5H); 4.6–4.0 m (4H); and 3.5–1.5 m+s (13H)
IR: 1685 cm$^{-1}$
Hydrochloride, melting point: 251°–255° C. (decomposition)

EXAMPLE 86

1-[(7-Fluoro-benzo-1,4-dioxan-2-yl)-methyl]-4-(6-chlorobenzimidazol-2-on-1-yl)-piperidine Free base, melting point: 233°–235° C.
NMR: 10.8 s (1H); 7.4–6.8 m (6H); 4.6–4.0 m (4H); and 3.5–1.5 m (10H)
IR: 1685 cm$^{-1}$ Hydrochloride, melting point: 227° C. (decomposition)

EXAMPLE 87

1-[(7-Fluoro-benzo-1,4-dioxan-2-yl)-methyl]-4-(7-chlorobenzimidazol-2-on-1-yl)-piperidine Free base, melting point: 174°–176° C.
NMR: 10.8 s (1H); 7.4–6.8 m (6H); 4.6–4.0 m (4H); and 3.5–1.5 m (10H)
IR: 1685 cm$^{-1}$
Hydrochloride, melting point: 242°–251° C.

EXAMPLE 88

1-[(7-Fluoro-benzo-1,4-dioxan-2-yl)-methyl]-4-(5,6-dichlorobenzimidazol-2-on-1-yl)-piperidine Free base, melting point: 235°–237° C.
NMR: 10.8 s (1H); 7.5–6.7 m (5H); 4.6–4.0 m (4H); and 3.5–1.5 m (10H)
IR: 1685 cm$^{-1}$
Hydrochloride, melting point: 258°–261° C. (decomposition)

EXAMPLE 89

1-[(7-Fluoro-benzo-1,4-dioxan-2-yl)-methyl]-4-(5-trifluoromethyl-benzimidazol-2-on-1-yl)-piperidine Free base, melting point: 115°–118° C.
NMR: 10.8 s (1H); 7.7–6.8 m (6H); 4.6–4.0 m (4H); and 3.5–1.5 m (10H)
IR: 1685 cm$^{-1}$
Hydrochloride, melting point: 170°–175° C.

EXAMPLE 90

1-[(6-Fluoro-benzo-1,4-dioxan-2-yl)-methyl]-4-(5-methoxybenzimidazol-2-on-1-yl)-piperidine NMR: 10.9 s (1H); 7.1–6.2 m (6H); 4.6–4.0 m+s (7H); and 3.5–1.5 m (10H)

IR: 1685 cm$^{-1}$

EXAMPLE 91

1-[(7-Fluoro-benzo-1,4-dioxan-2-yl)-methyl]-4-(5-methoxybenzimidazol-2-on-1-yl)-piperidine NMR: 11.0 s (1H); 7.1–6.2 m (6H); 4.6–4.0 m+s (7H); and 3.5–1.5 m (10H)

IR: 1685 cm$^{-1}$

We claim:

1. A compound of the formula

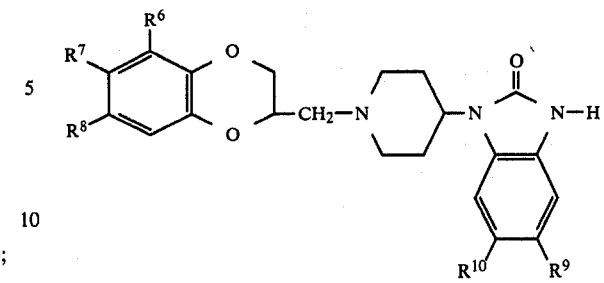

or a physiologically acceptable salt thereof, in which $R^6$ denotes hydrogen or methyl, $R^7$ and $R^8$ independently of one another denote hydrogen, fluorine, chlorine or methyl, $R^9$ denotes fluorine, chlorine, methyl or methoxy and $R^{10}$ denotes hydrogen or methyl.

2. A compound or salt as claimed in claim 1, in which $R^6$, $R^7$ and $R^{10}$ denote hydrogen, $R^8$ denotes hydrogen or fluorine and $R^9$ denotes fluorine, chlorine, methyl or methoxy.

3. The compound or salt as claimed in claim 2, wherein $R^8$ is hydrogen and $R^9$ is chlorine.

4. The compound or salt as claimed in claim 2, wherein $R^8$ is hydrogen and $R^9$ is methyl.

5. The compound or salt as claimed in claim 2, wherein $R^8$ is fluorine and $R^9$ is methyl.

6. The compound or salt as claimed in claim 2, wherein $R^8$ is hydrogen and $R^9$ is fluorine.

7. The compound or salt as claimed in claim 2, wherein $R^8$ is hydrogen and $R^9$ is methoxy.

8. A medicament for modifying psychotic behavior containing a neuroleptically active amount of a compound or salt as claimed in claim 1, together with a pharmaceutically acceptable carrier therefor.

* * * * *